US006485443B1

(12) United States Patent
Garth

(10) Patent No.: US 6,485,443 B1
(45) Date of Patent: Nov. 26, 2002

(54) SEATING PRODUCTS WITH SELF POWERED DYNAMIC MASSAGE UNITS

(76) Inventor: Geoffrey C. Garth, 34-57th Pl., Long Beach, CA (US) 90803

( * ) Notice: Subject to any disclaimer, the term of this patent is extended or adjusted under 35 U.S.C. 154(b) by 0 days.

(21) Appl. No.: 09/419,660

(22) Filed: Oct. 18, 1999

(51) Int. Cl.[7] .................................................. A61M 1/00

(52) U.S. Cl. ........................... 601/98; 601/99; 601/115; 601/116

(58) Field of Search .............................. 601/89, 90, 91, 601/92, 97, 98, 99, 115, 116, 118, 119

(56) References Cited

U.S. PATENT DOCUMENTS 5,348,529 A * 9/1994 Veltri .......................... 601/99

* cited by examiner

*Primary Examiner*—Michael A. Brown
*Assistant Examiner*—Benjamin K. Koo
(74) *Attorney, Agent, or Firm*—Allen A. Dicke, Jr.

(57) ABSTRACT

Massage pressure devices are fitted onto a chair which has a rocking back, either conventional rocking chair or an office chair with pivoted an spring-loaded back, so that massage is applied to the back of a person seated in and rocking the chair. The massage pressure devices are rollers or pads which are mounted so that the amount of massage pressure and the position of the massage pressure are adjustable in accordance with the user's desires. The massage pressure drive mechanism includes a reference to the base so that the massage pressure devices are driven up and down the chair back as the chair back rocks back and forth. In a conventional rocking chair, the truck carrying the massage pressure rollers is adjustable in both pressure of the devices against the back and the position thereof. In an office-style chair, the position of the pressure devices and the force of the massage pressure devices against the chair back are controlled by adjusting the position of the mounting tube and the spring extension.

8 Claims, 6 Drawing Sheets

SEATING PRODUCTS WITH SELF POWERED DYNAMIC MASSAGE UNITS

FIELD OF THE INVENTION

This invention is directed to a chair having a flexible back support with massage rollers pressing forward to flex the back support. A drive linkage drives the rollers up and down the back support as the back is rocked.

BACKGROUND OF THE INVENTION

Most chairs support the principal weight of the person by posterior engagement on the seat of the chair. However, a back support is necessary for long-term, comfortable sitting. Both the seat and the chair back are preferably configured to properly engage the person so that loading is most comfortable. Many office-type chairs have adjustments to achieve this end. Many chairs are configured so that at least the back rocks with respect to the floor. In the class known as "rocking chairs," the seat an back are fixed with respect to each other. They are supported on rockers which permit the chair structure to rock with respect to the floor. In other cases, particularly office chair the structure of the chair may be non-rocking with respect to the floor, but the back can rock back and forth with respect to the seat. Various levels of comfort are achieved by providing the rocking feature.

It would be desirable to utilize the rocking motion of the back to cause therapeutic motion of rollers working on the person's body through the back of the chair.

SUMMARY OF THE INVENTION

In order to aid in the understanding of this invention, it can be stated in essentially summary form that it is directed to a chair with massage rollers. The chair is configured so that rollers make contact with the portions of an individual seated in the chair through the chair back. The rollers are connected to the non-rocking part of the chair, which is stationary so that the rollers move against a portion of the chair to thus cause manipulation of the muscles of the seated person.

It is, thus, a purpose and advantage of this invention to provide a chair with massage pressure devices such as rollers or pads which act through the chair onto the person seated in the chair as the person rocks in the chair.

It is another purpose and advantage of this invention to provide a massage roller structure which is useful in a conventional rocking chair or any kind of chair where the seat rocks with the back as well as with a chair where the back is pivoted with respect to the seat, with the massage rollers moved by the relative motion of the back to cause massage activity.

It is another purpose and advantage of this invention to provide massage rollers or pads and mounting therefor which can be attached an already existing chair to add the feature of massage thereto.

It is a further purpose and advantage of this invention to provide a chair with massage rollers wherein the height and/or the force of the massage rollers against the chair can be adjusted.

It is a further purpose and advantage of this invention to provide massage rollers, in association with a chair with a rocking back, of such adjustable nature as to permit adjustment of the roller position and/or the roller pressure.

It is a further purpose and advantage of this invention to supplement or replace the spring or bias mechanism which is used in many office chairs to allow the back to return after flexing backward under a load and utilize that motion to drive a massage mechanism.

It is another purpose and advantage of this invention to provide massage rollers which can be attached to a suitable chair with rocking back so as to convert the chair into one having massage rollers actuated by rocking of the chair back.

Other purposes and advantages of this invention will become apparent from a study of the following portion of the specification, the claims and the attached drawings.

DESCRIPTION OF THE PREFERRED EMBODIMENTS

Figure 1:
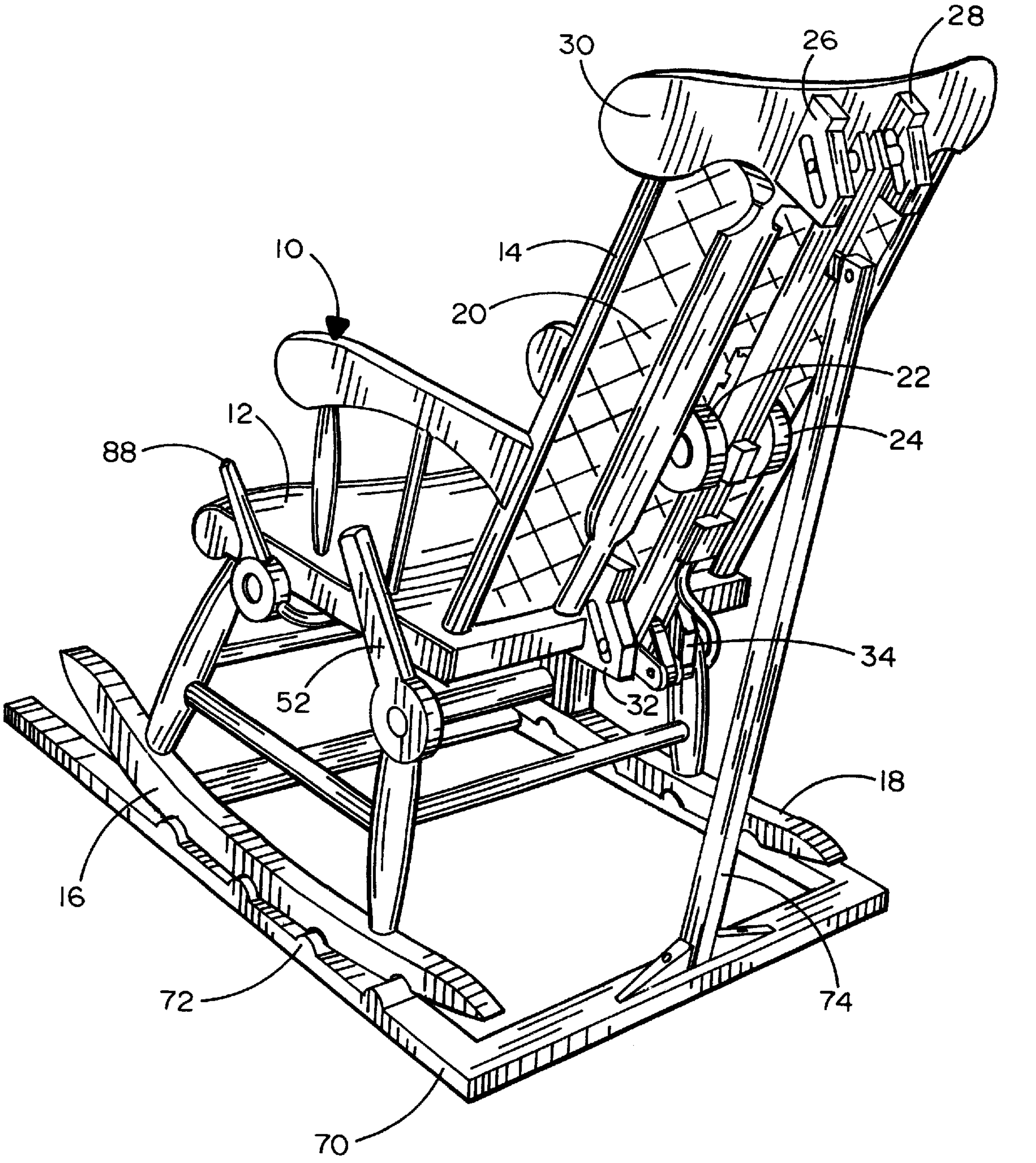
FIG. 1 is a rear perspective view of the first preferred embodiment of this invention showing the massage rollers in association with the chair back.
Figure 2:
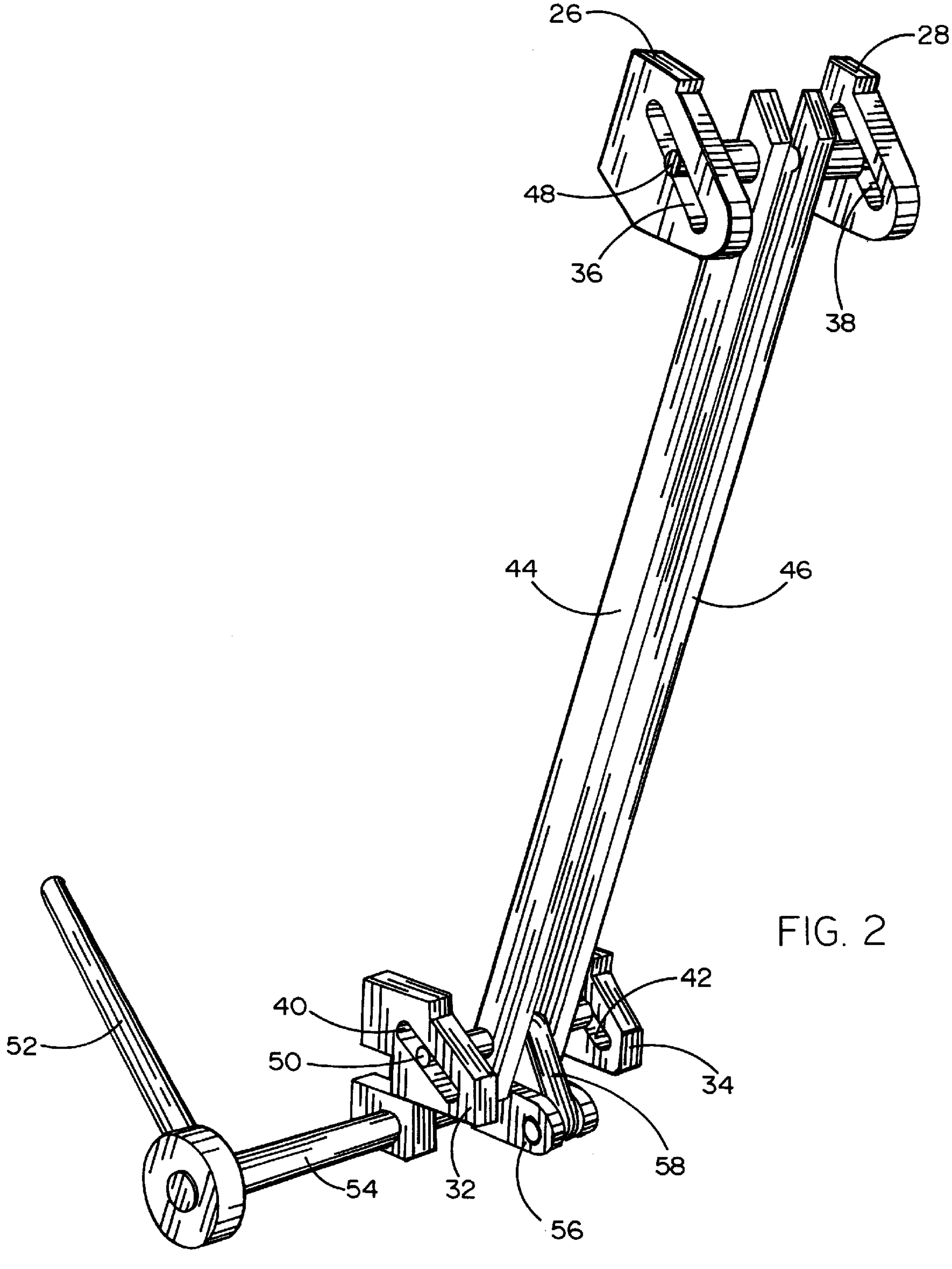
FIG. 2 is a rear-left side perspective of the mechanism for moving the track closer to the chair back.
Figure 3:
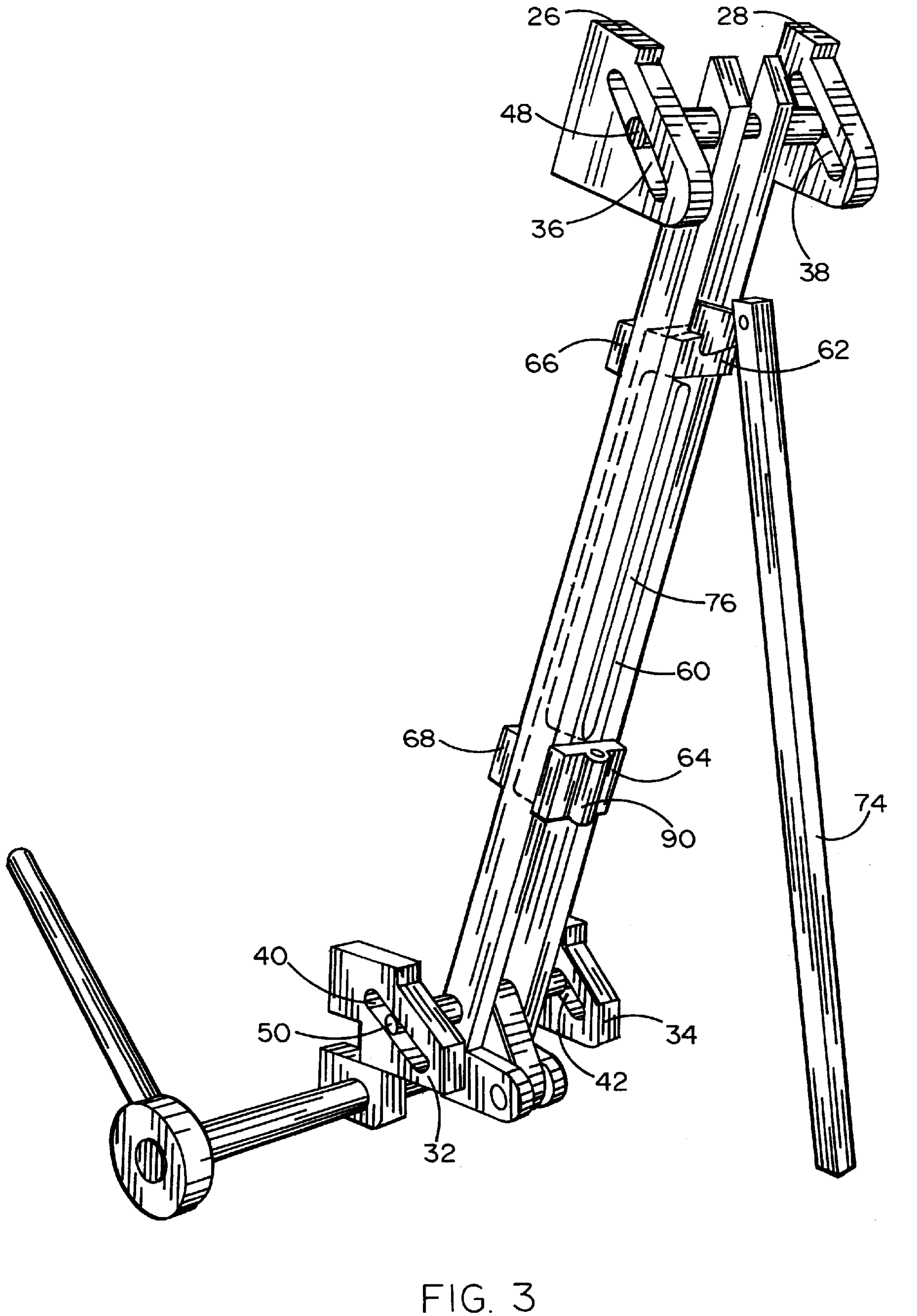
FIG. 3 is a similar view showing the carriage being mounted on the track.

FIG. 1 is a left-rear perspective view of a rocking chair 10 which is of fairly conventional nature. It has a seat 12 and a back 14. The seat is supported upon rockers 16 and 18 so that the chair may be rocked by the occupant. The back 14 is formed of a plurality of uprights with soft, flexible cushion material 20 there against. In accordance with this invention, the chair 10 is provided with massage rollers 22 and 24, which roll up and down the back. The positioning and driving of the massage rollers 22 and 24 is provided by the massage roller drive mechanism, which is illustrated in various details in FIGS. 1, 2, 3, 4 and 5. The motion of the massage rollers flexes the chair back to act upon the person employing the chair.

Upper cam brackets 26 and 28 are secured to the upper back cross piece 30 of the chair, as seen in FIG. 1. Lower cam brackets 32 and 34 are secured to the back of the chair seat 12. Each of the brackets is substantially the same. The upper cam brackets have cam slots 36 and 38 therein, while lower cam brackets 32 and 34 have lower cam slots 40 and 42 therein. The upper cam slots lie in the same plane, while the lower cam slots also lie in their own plane. The cam slots are parallel to each other and are inclined on an upward/forward slope.

Tracks 44 and 46 are positioned between the brackets 26 and 28 and between the brackets 32 and 34. Upper pin 48 is attached through the upper end of both tracks 44 and 46 to maintain them in properly spaced relationship and to engage in the upper slots 36 and 38. Similarly, lower pin 50 is attached through both tracks 44 and 46, holds them in spaced relationship, and passes through the lower cam slots 40 and 42. It is thus seen that upward motion of the tracks causes the tracks to move forward with respect to the chair.

Hand lever 52 is mounted on shaft 54, which is pivoted on blocks secured to the seat of the chair. Arm 56 is fixed to shaft 51, and link 58 is pivotally mounted on the end of arm 56 and on lower cross pin 50. Thus, forward thrust on the hand lever 52 raises arm 56 and moves the tracks upward and forward in accordance with the defined cam surfaces.

Carriage 60 (see FIGS. 3 and 4) is an elongated rectangular structure which slides between the rails. Upper and lower rear caps 62 and 64 and upper and lower front caps 66 and 68 constrain the carriage to sliding motion between the rails.

Referring to FIG. 1, rocking chair 10 rocks upon a base 70. A plurality of keys, one of which is shown at 72, keep the chair and base in alignment. Another alignment device would be to connect the base and rockers with flexible straps. The base acts as a reference surface during rocking of the chair with respect thereto. A driver 74 is pivotally mounted on the rear of the base 70 and, at its upper end, is pivotally mounted on the upper rear cap 62. When the chair 10 is rocked with respect to the base, the driver 74 moves carriage 60 up and down in its slot between the rails.

Figure 5:
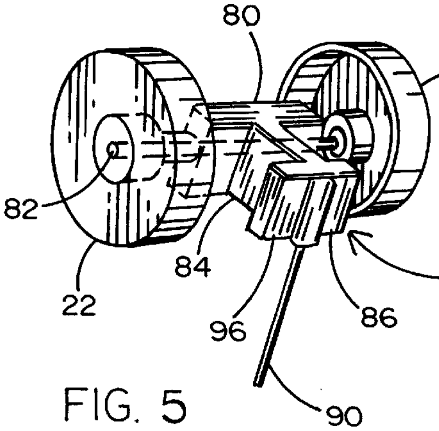
FIG. 5 is a perspective view of the truck with its massage rollers.
Figure 4:
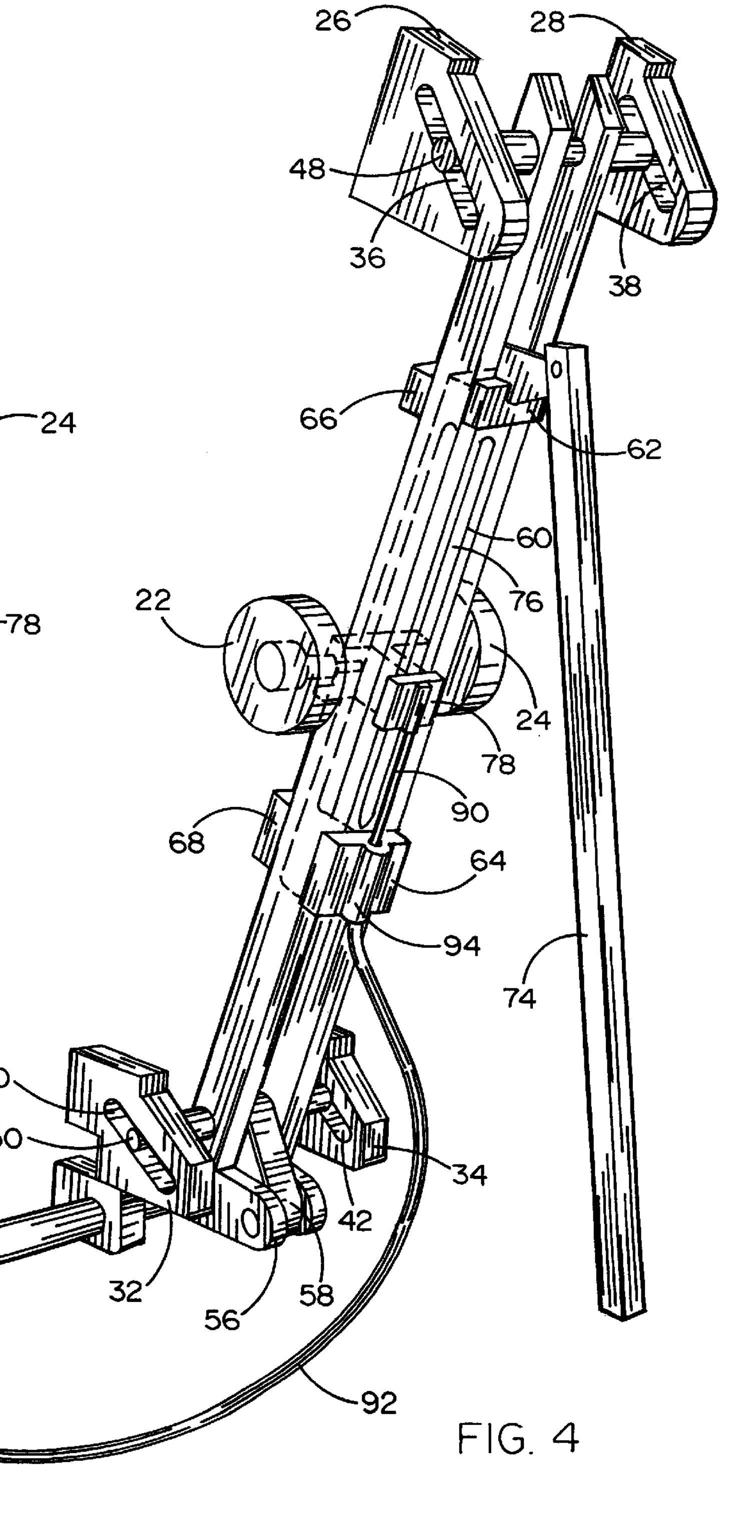
FIG. 4 is a similar view showing the truck mounted on the carriage to complete the assembly.
Figure 4:
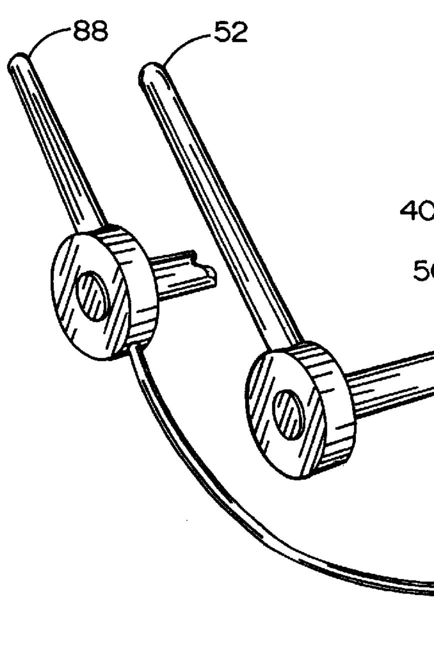

The carriage 60 has an elongated slot 76 down its length which extends through the carriage from front to back. Truck 78, see FIGS. 4 and 5, is mounted in slot 76 to be positionable along the length thereof. Truck 78 is T-shaped with its upper cross bar 80 carrying axel 82 upon which the massage rollers 22 and 24 are mounted. The shank 84 of the truck extends through the slot 76. The truck is retained in its slot by lower cross bar 86, which engages on the rear side of carriage 60. The truck is limited on its motion by the length of the slot 76 in carriage 60, as well as by the upper and lower caps on the carriage.

Control of the position of the truck on the carriage is managed by a flexible wire controller. Hand lever 88 controls the position of flexible wire 90 within flexible sheath 92. The flexible sheath is secured by clamp 94 on lower rear cap 64. The flexible wire 90 is attached to the truck by means of clamp 96. Thus, when the hand lever 88 is manipulated, the wire 90 moves the truck up and down on the carriage.

A person utilizing the rocking chair 10 sits therein. By moving the hand lever 52, he moves the tracks 44 and 46 and the massage rollers 22 and 24 forward and back to achieve the desired amount of flexure of the flexible chair back material and the pressure directed against the person's back. He manipulates hand lever 88 to move the massage rollers 22 and 24 to the desired massage position up and down his back. Rocking of the chair with respect to the base; that is, actuating the driver, causes the massage rollers to move with respect to the back and create a therapeutic massage condition. Preferably, the massage rollers act through a flexible chair back. If preferred, slots in the chair back could permit direct application of the rollers to the person's back.

Figure 6:
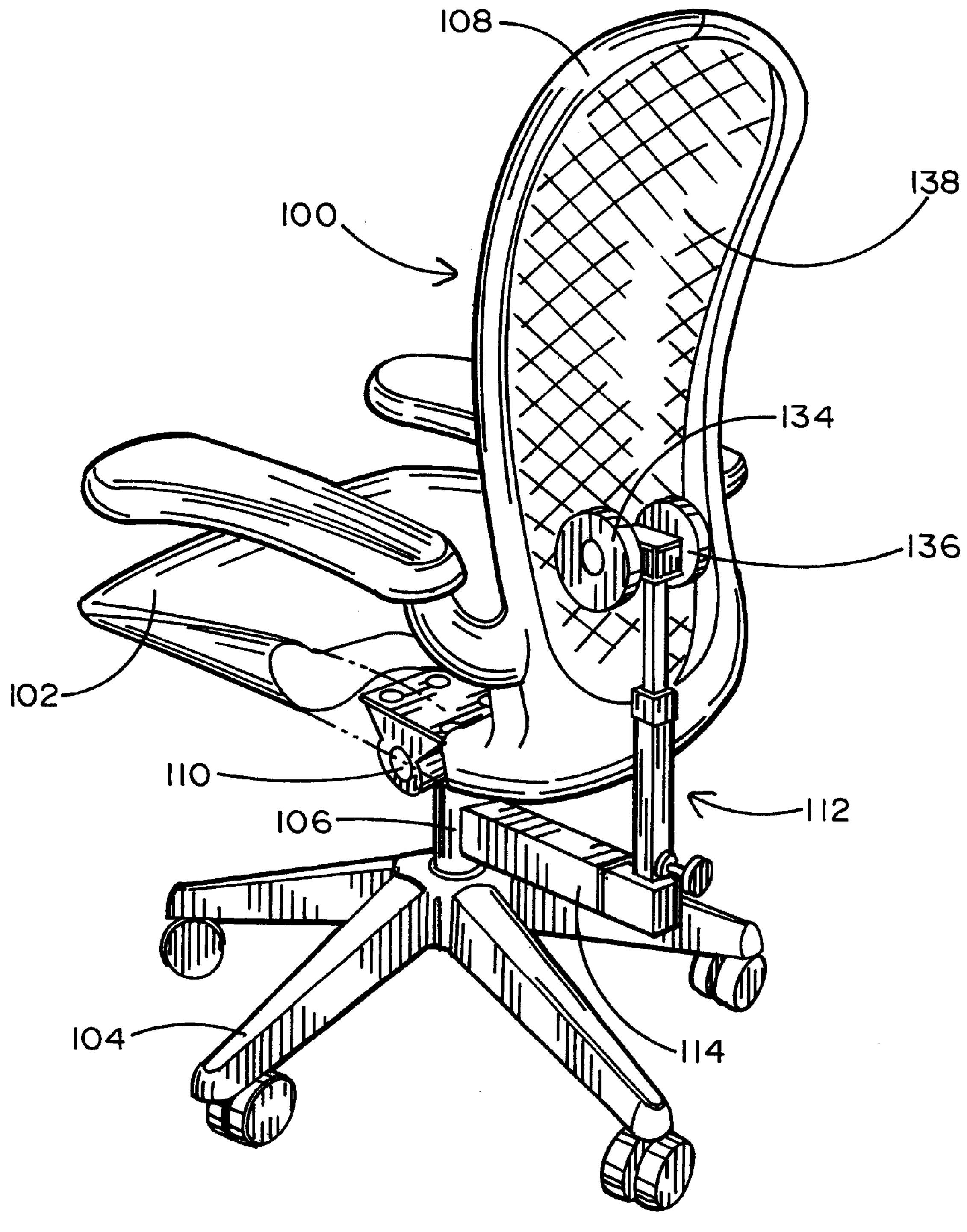
FIG. 6 is a perspective view of an office chair showing the manner in which the massage rollers of this invention can be fitted thereto.
Figure 7:
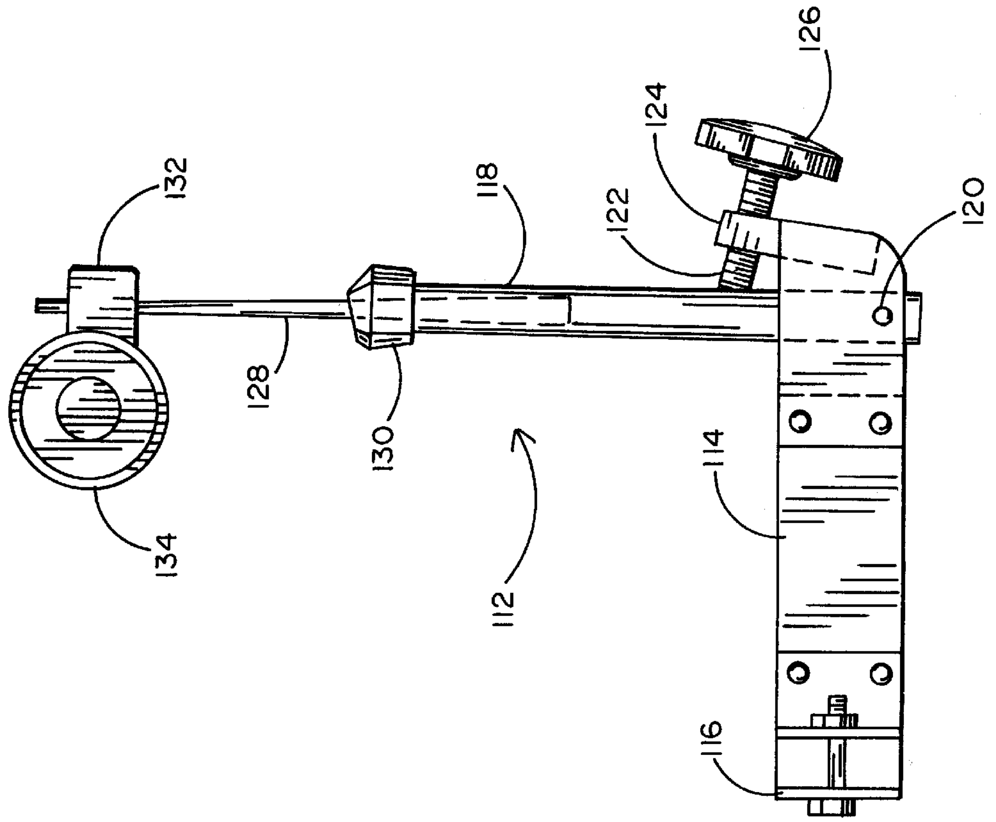
FIG. 7 is a side-elevational view of the massage roller structure.

Another preferred embodiment of the chair back with massage rollers in accordance with this invention is shown in FIGS. 6 and 7. Chair 100 has a seat 102, which is mounted on a base 104. The base 104 is of the type often found in office chairs where is a plurality of casters mounted under the base. A pin 106 extends upward from the base. The pin 106 rotates with the chair but does not rock with respect to the base. The chair 100 may have its back 108 and its seat 102 fixed together, in which case the seat-plus back assembly is pivotally mounted to rock on the base. That is the case in the present structure where pivot pin 110 is a pin which is transverse to the seat and permits the seat plus-back assembly to rock backward with respect to the base. In other cases, the seat does not rock, but the back is pivoted to swing backward under load. In the usual chair, adjustable springs are provided to return the back to the upright position. The action which drives the massage rollers is the rocking of the back with respect to the base. In this structure, the back support springs are preferably part of the massage drive mechanism. The chair back is sufficiently flexible, or there are slots therein, so that the massage rollers can act therethrough to provide massage action to the seated person.

The massage roller mechanism 112 suitable for use with the chair 100 is shown in FIGS. 6 and 7. Bracket 114 extends rearwardly under the seat and is secured in place on the post 106 by means of clamp 116. The clamp 116 permits the massage roller mechanism to be after-mounted on chairs of suitable configuration. On the other hand, instead of a clamp 116, the bracket 114 may be permanently mounted on the chair post during its original manufacture.

Massage roller mounting tube 118 is pivoted on pivot pin 120 on bracket 114. Adjustment screw 122 is threaded through boss 124. The adjustment crew 122 carries manual knob 126, which limits the rearward position of the mounting tube 118 with respect to bracket 114.

Spring 128 is trapezoidal in side-elevational view, as seen in FIG. 7. It is rectangular in rear view and is rectangular in cross section. The spring 128 is a flat leaf spring which extends down into the tube 118. Cap 130 engages the spring to hold it in place. When there is no load on the spring, the spring can be manually moved up and down so as to extend different distances out of the top of the mounting tube 118. The cap 130 holds it in place until the next manual adjustment. Truck 132 carries back massage rollers 134 and 136 pivotally mounted thereon. The massage rollers extend forward and engage against the fabric 138 of the back 108. The fabric is flexible so that the massaging action of the rollers can be felt therethrough. Spring 128 extends upward through a rectangular opening in truck 132. The fit is such that the truck can be adjusted up and down on spring 128 when there is no forward load on the massage rollers. The position of the truck on the spring 128 can be selected, and the truck remains in position until further manual adjustment.

The height of the massage rollers 134 and 136 is set in accordance with the desires of the user to massage a desired area. Thus, the up and down position of the massage rollers is adjusted by the user in accordance with his comfort. This is the position of the truck above the mounting tube 118. An additional variable is provided by the spring 128. The greater the amount of spring exposed between the mounting tube and the truck, the greater the deflection for the same force. Since the spring 128 is tapered, different portions of it have a different spring rate. Thus, presuming a fixed starting position for the truck 132, moving the spring downward in both the truck 132 and mounting tube 118 provides a lower spring rate. Conversely, raising the spring 128 places a thicker portion of the spring in the active bending position between the top of the mounting tube and the truck to thus stiffen the structure counteracting the increased flexibility associated with the increased length of the spring and provide a heavier force of the massage rollers against the chair back fabric 138. In addition, truck 132 can be positioned upward or downward on the spring 128 to further adjust the degree of force delivered by the massage rollers.

Figure 8:
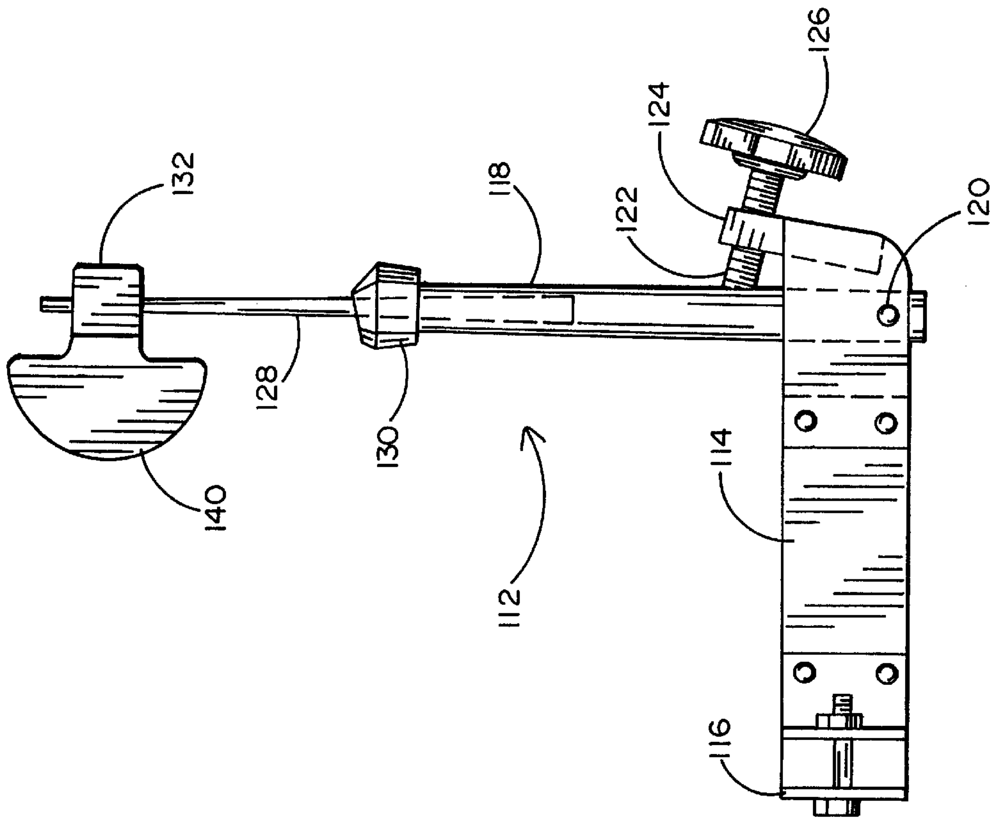
FIG. 8 is a side elevational view of a massage pad structure which can be used alternatively to the massage roller shown in FIGS. 5 and 7.

The massage pad 140 shown in FIG. 8 can be used alternatively to the massage rollers shown in FIGS. 5 and 7.

The rollers and the massage pad can be considered as massage pressure devices.

This invention has bee described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A massage pressure device system for a chair having a base and having a rocking flexible back, comprising:

a truck, at least one massage pressure device mounted on said truck, said truck being positionable behind the rocking flexible back of the chair an arm for mounting on the chair base, and a spring carrier on said arm, a spring interconnecting said spring carrier and said truck, said spring being movably mounted with respect to said spring carrier to selectively position said truck up the back of the chair so as to drive said at least one massage pressure device up and down the back of said chair when the back is rocked backward and forward with respect to said base and said spring provides the force of said massage pressure device against the flexible back of the chair.

2. The massage pressure device system of claim 1 wherein said spring has a top and said truck is selectively positionable below said top of said spring to control pressure of said at least one massage pressure device against the back of the chair.

3. The massage pressure device system of claim 2 wherein said spring has a non-uniform cross section so that selected spring rate can be achieved by selectively positioning said spring with respect to said spring carrier and said truck.

4. The massage pressure device system of claim 1 wherein said spring carrier is adjustably mounted with respect to said arm so that the pressure of said at least one massage pressure device against the chair back can be controlled.

5. A massage pressure device system for a chair having a base and having a back which rocks with respect to the base, comprising:

a mounting bracket for attachment to the base;

a spring carrier movably mounted on said bracket;

a spring to provide resilient mounting of said massage pressure device, said spring being mounted to extend from said spring carrier, said spring providing all massage pressure;

a massage pressure device mounted on said spring for engaging against the back of the chair and for engaging through the back of the chair the back of a person sitting in the chair and for moving up and down as the back of the chair is rocked with respect to the base of the chair to massage the back of a person sitting in the chair and rocking the chair, said massage pressure device being mounted on said spring so that spring deflection causes resilient force of said massage pressure device against the chair back, said massage pressure device being adjustably mounted with respect to said bracket so that the amount of chair back deflection and the amount of force required to achieve that deflection can be selected.

6. The massage pressure device system of claim 5 wherein there is an adjustable stop engaged between said bracket and said spring carrier so that adjustment of said stop adjusts the amount of force required to achieve that amount of chair back deflection.

7. The massage pressure device system of claim 6 wherein there are first and second massage pressure rollers mounted on a truck and said truck is adjustably mounted on said spring and said spring is adjustably mounted in said spring carrier so that the amount of spring deflection can be adjusted.

8. The massage pressure device system of claim 7 wherein said spring is a tapered flat spring so that spring rate can be adjusted by selecting the portion of said tapered flat spring exposed between said spring carrier and said truck.

* * * * *